United States Patent [19]

Emerson

[11] Patent Number: 6,124,275
[45] Date of Patent: Sep. 26, 2000

[54] METHODS AND COMPOSITIONS FOR CONTROLLING A PEST POPULATION

[75] Inventor: Ralph W. Emerson, Davis, Calif.

[73] Assignee: Summus Group, Ltd., Woodland, Calif.

[21] Appl. No.: 09/301,954

[22] Filed: Apr. 29, 1999

Related U.S. Application Data

[63] Continuation-in-part of application No. 09/071,750, May 1, 1998, abandoned.

[51] Int. Cl.$^7$ .......................... A01N 37/36; A01N 31/08; A01N 37/10
[52] U.S. Cl. ...................... 514/159; 424/DIG. 10; 514/163; 514/544; 514/731; 514/919; 514/975
[58] Field of Search .................. 514/975, 532, 514/533, 543, 544, 546–548, 557, 568, 576, 577, 717, 728, 734–737, 159, 163, 731, 919; 424/405, 406, DIG. 10; 206/459.5

[56] References Cited

U.S. PATENT DOCUMENTS

| | | | |
|---|---|---|---|
| 2,394,916 | 2/1946 | Jones | 167/45 |
| 3,169,849 | 2/1965 | Lemin | 71/2.6 |
| 3,681,045 | 8/1972 | Gough | 71/107 |
| 3,811,932 | 5/1974 | Hubele | 514/586 |
| 3,944,411 | 3/1976 | Rohr | 71/107 |
| 3,983,214 | 9/1976 | Misato et al. | 424/180 |
| 4,562,794 | 1/1986 | Speckman | 119/651 |
| 4,621,090 | 11/1986 | Iwata et al. | 514/332 |
| 4,666,940 | 5/1987 | Bischoff, et al. | 514/544 |
| 4,800,196 | 1/1989 | Nomura et al. | 514/159 |
| 4,940,583 | 7/1990 | Thompson | 424/195.1 |
| 5,017,615 | 5/1991 | Workman | 514/560 |
| 5,358,966 | 10/1994 | James, Jr. et al. | 514/615 |
| 5,395,616 | 3/1995 | Edwards et al. | 424/405 |
| 5,576,011 | 11/1996 | Butler et al. | 424/411 |
| 5,693,344 | 12/1997 | Knight et al. | 424/687 |
| 5,900,244 | 5/1999 | Howse | 424/405 |

OTHER PUBLICATIONS

FR002697133A1 (GERARD), Synergistic biocidal and biostatic compsns, active against eg bacteria, fungi and viruses—contg a sesquiterpene, eg pinene, and an aromatic cpd, eg carvacrol, APS,GPI,EPO, Abstract, Apr. 1994.

JP 05039203 A, Safe miticidal compositions having no residual toxicity, West online, file DWPI, abstract. (1993).

Matsumoto et al., JP01019004, Acaricides, insecticides, and insect repellants containing benzaldehyde or perilla aldehyde, STN/CAS online, file CAPLUS, abstract. (1989).

Database CA on STN, Abstract of Japan Patent No. 409124412, Kiyono et al., "Agent for Controlling Plant Hopper," May 13, 1997.

Brinck–Lindroth et al., "Control of the Human Head Louse with Disulfiram and Benzyl Benzoate Emulsions," Acta. Derm. Venereol., vol. 64, pp. 325–330, 1984.

Brown, "House Dust Mice Control with Acarosan–an Extreme test?", Clinical and Experimental Allergy, vol. 24, pp. 690–691, 1994.

Frances et al., "Laboratory Tests of Arthropod Repellents Against Leptotrombidium deliense–Noninfected and Infected with Rickettsia tsutsugamushi–and Noninfected L. fletcheri (Acari: Trombiculidae)," J. Med. Entomol., vol. 33, No. 2, pp. 232–235, 1996.

Frances, "Response of a Chigger, Eutrombicula hirsti (Acari: Trombiculidae) to Repellent and Toxicant Compounds in the Laboratory," J. Med. Entomol., vol. 31, No. 4, pp. 628–630, 1994.

*Primary Examiner*—John Pak
*Assistant Examiner*—Frank Choi
*Attorney, Agent, or Firm*—Cooley Godward LLP

[57] ABSTRACT

The invention is directed to a method for controlling a pest population using a composition comprising a benzyl ester of an aromatic acid or aliphatic acid or a salicylate. Methods and compositions for controlling a pest population are provided. The compositions comprise a benzyl ester of an aromatic acid or aliphatic acid or a salicylate. The composition can include at least one fatty-acid ester to increase the pesticidal activity. The subject method controls the population of pests such as plant pests or pests infesting a mammal by contacting the pests with the composition. The subject method reduces the environmental and health hazards in pest control by minimizing the toxicity of the subject composition.

7 Claims, No Drawings

METHODS AND COMPOSITIONS FOR CONTROLLING A PEST POPULATION

CROSS REFERENCE TO RELATED APPLICATION

This application is a continuation-in-part of U.S. Ser. No. 09/071,750, filed on May 1, 1998, now abandoned.

BACKGROUND

1. Field of the Invention

This invention relates to methods and compositions for controlling a pest population. This invention is exemplified by a method for controlling growth of thrips, aphids, and spider mites on plants using a composition comprising a pest population controlling amount of a benzyl ester of an aromatic acid or aliphatic acid or a salicylate derivative.

2. Background of the Invention

Pests such as insects, arachnids, fungi, mites, and nematodes are detrimental to man. Pests include pathogenic organisms which infest mammals and plants; some of these pests can spread disease as disease vectors. The pathogenic organisms which infest plants and cause economic loss of plant crops include fungi, insects, arachnids, gastropods, and nematodes. The pathogenic organisms which infest animals include ticks, mites, fleas, and mosquitoes. Other pests include cockroaches, termites and ants.

Methods for controlling plant pathogens include spraying plants with fungicides on a 6–7 day schedule when environmental conditions favor disease development. These methods are typically used for controlling fungal infestations such as rust and powdery mildew. Typical fungicides used include heavy metals such as copper, mercury and arsenic, as well as organophosphorous and organic chlorine compounds. These compounds are often not satisfactory because of their potential for polluting the soils, their strong physiological effects on the plants, their residual toxicity in food crops, their high animal toxicity, and the potential hazards to workers using them.

Other methods of controlling pests such as insects and soil pests, such as nematodes and phylloxera, often involve the use of organophosphates, pyrethrum, pyrethroids (synthetic pyrethrum), mineral oil, oil, methoprene, and Baccillus thuringiensis israelensis crystal protein. Generally, these compounds are applied directly onto the pest population to control the organisms. Many of these compositions are toxic to large animals, including man, in addition to being toxic to insects or fungi. Further, many compositions that function as pesticides accumulate in the environment to levels considered to be unsafe. In addition, many of these compositions have been found to contaminate natural resources such as drinking water. Such problems have led the government to ban the use of many pesticides, including DDT, Chlorodane, Lindane, Aldrin, Heptachlor, Dieldrin, and Mirox. Other compositions, those still in use, present varying degrees of unwanted toxicity. Besides unwanted toxicity, presently-known pesticides have other problems. They tend to be complex and expensive to produce. It is often necessary to apply multiple pesticides to obtain satisfactory control of a variety of pests.

Biorational pesticides also are used in controlling pathogenic and pest organisms. A method of induction of systemic resistance to powdery mildew in cucumber by phosphates has been described (Reuvenl, et al. *Biol. Agric. & Hort.* (1993) 9:305–315). The phosphate salts serve the dual purpose of acting as a foliar fertilizer and as an agent for inducing resistance to pathogenic organisms. However, excessive use of phosphates produces agricultural runoffs that can cause water pollution. Methods for controlling powdery mildew and black spot on roses have been described (*Plant Disease* (1992) 76:247–251) which use sodium bicarbonate and light paraffinic petroleum oil. However, the bicarbonate salts are fungicidal only at pH 8.6 and are non-fungicidal at pH 6.0. The bicarbonate salts also can be phytotoxic as a function of environmental conditions at the time of treatment.

Also used for the control of powdery mildew in the field are anti-transpirants. Anti-transpirants are chemicals applied directly to a plant which reduce the rate of transpiration or water loss by the plant. Anti-transpirants form a film on a plant surface which acts as a barrier against invading pests. The anti-transpirant formulations are reported to have low mammalian toxicity, however, because the anti-transpirant controls pests through the formation of a protective barrier, it is useful only as a means of prevention rather than as a treatment of an already infected plant.

Therefore, it is of interest to identify and develop compositions and methods for controlling the growth of pathogenic and pest organisms which use formulations derived from natural products or are known to have lower environmental toxicity than the formulations currently in use, yet are effective in controlling insects and other pathogens without damaging a treated plant and/or plant part or a host tissue. It also is of interest to develop a new composition which is effective against more than one kind of pest so as to decrease the need for application of multiple pest control agents.

Relevant Literature

U.S. Pat. No. 3,983,214 discloses a fungicidal composition containing as an active ingredient, a $C_{8-18}$ sucrose fatty-acid ester, and at least an adjuvant selected from the group consisting of a solid-carrier, a liquid-carrier, an emulsifying agent, a dispersing agent, and a surface-active agent.

Frances (*J. Med. Entomol.* (1994) 31(4):628–630) reports that *E. hirsti* (chiggar mite) larvae exposed to cloth treated with an ethanol solution of 5% benzyl benzoate caused 100% knockdown of test larvae in <3 minutes.

Frances et al. (*J. Med. Entomol.* (1996) 33(2):232–235) disclose the toxicant effect of benzyl benzoate for scoring "knock-down" of a mite following exposure of chiggar larvae on white cotton fabric treated with benzyl benzoate in an ethanol formulation.

Brink-Lindroth, et al. (*Acta Derm. Venereol* (1984) 64:325) report killing human head lice eggs by applying benzyl benzoate (22.5 g) as a thin layer on the eggs, while Brown (*Clin. Exp. Allergy* (1994) 24:690) discloses a method of controlling the house dust mite with Acarosan.

OBJECTS OF THE INVENTION

One object of this invention is to provide a new family of pesticides based on easily obtainable compounds which are benzyl esters of an aromatic acid or aliphatic acid or a salicylate derivative.

Another object of this invention is to provide a new family of pesticides using naturally-occurring compounds.

Yet another object of this invention is to provide a new family of pesticides having low toxicity to ornamental and agricultural plants, domesticated animals and wildlife, and humans when used at a pesticidally effective level.

Other objects may be apparent to one of skill in the art upon reading the following specification.

SUMMARY OF THE INVENTION

The present invention is directed to a method for controlling a pest population, such as by eliminating or deterring the growth of the pest population, using a composition containing a pesticidally effective amount of a benzyl ester of an aromatic acid or aliphatic acid or a salicylate derivative. The method finds use in controlling pest populations and in preventing infestation of a host with a pest, where the pest population is a plant pest population or a pest population that infests animals. The method of the invention includes the step of contacting the pest population with a pesticidally effective amount of a composition comprising a compound of the invention in combination with an agriculturally-acceptable carrier.

The invention is also directed to a method for preventing infestation of a host with a pest by contacting the host, such as by spraying, with a composition comprising a compound of the invention in combination with an agriculturally-acceptable carrier in an amount sufficient to prevent infestation.

The invention also provides a composition comprising a pesticidally active compound of the invention, and optionally a surfactant. The present invention is also directed to uses for such compositions in methods for preventing infestation of a host with a pest, for treating a fungal infestation of a fruit bearing plant in need thereof, and for treating an arthropod infestation on an ornamental plant in need thereof.

The invention also pertains to an article of manufacture comprising a container in association with instructions and/or a label indicating that the subject composition can be used to control pests, i.e., used as a pesticide and holding a composition comprising an agriculturally-acceptable carrier and a pesticidally active compound of the invention.

DETAILED DESCRIPTION

Methods and compositions for controlling a plant or mammalian pest population are provided. The compositions used comprise a benzyl ester of an aromatic acid or aliphatic acid or a salicylate derivative in a formulation, which is either non-phytotoxic or non-dermal sensitive if the intended application is to the tissue of the host. The pest population is a pathogenic organism population which often spreads disease and/or damages the host, and includes plant pests and those that infest mammals.

As used herein the terms "pest", "pest organism" and "pest population" refers to organisms and microorganisms, including pathogens, that negatively affect plants or animals by colonizing, attacking or infecting them. This includes organisms that spread disease and/or damage the host and/or competes for host nutrients. These organisms include, by way of illustration, and not limitation: insects such as fleas, mosquitoes, bees such as yellow jackets and wasps, cockroaches including the American and German cockroach, termites, houseflies and silverleaf whiteflies (*Besimsai argentifolii*), leaf hoppers such as the grape or potato leafhoppers (Cicidellidae), cabbage looper (Lepidoptera), ants such as the pharaoh ant, argentine ant, carpenter ant and fire ant, stink or lygus bugs, leafminers (*Liriomyza trifollii*), western flower thrips (*Frankliniella occidentalis*) and sucking or chewing insects such as thrips and aphids such as melon aphids (*Aphis gossypii*) and black bean aphids (*Aphis fabae*); arachnids such as spiders, ticks and plant mites, including two-spotted spider mites (*Tetronmychua urticae*), McDaniel mites, Pacific mites and European mites; gastropods such as slugs and snails; fungi such as powdery mildew including cladosporium, strawberry powdery mildew, rusts, botrytis, ergots, blight, downy mildew, eutypa, leaf spot, smut, Chytridimycota, Zygomycota, Asomycota, ringworm, rhizopus, rhizoctonia, pythium and erwinia; nematodes; and bacteria. The term "pest" specifically does not include lice and chiggar mites (trombiculid mites).

The present invention provides very efficacious pesticides which, in its preferred aspect, are designated as biorational. A biorational pesticide is a chemical substance of natural origin that can be synthesized. The preferred pesticides of the present invention have a lethal effect on specific pest targets. Unlike the bulk of currently available pesticides on the market, the preferred compositions have active ingredients that have been proven to be substantially non-toxic to man and domestic animals and which have minimal adverse effects on wildlife and the environment.

The efficacy of the subject composition is monitored by determining the mortality of or damage to the pest population, i.e., by determining its adverse effect upon treated pests. This includes damage to the pests, inhibition or modulation of pest growth, inhibition of pest reproduction by slowing or arresting its proliferation, or complete destruction/death of the pest, all of which are encompassed by the term "controlling". The term "pesticidally effective amount" is an amount of the compound of the invention, or a composition containing the compound, that has an adverse affect on at least 25% of the pests treated, more preferably at least 50%, most preferably at least 70% or greater. Preferably, an "effective pest-inhibiting amount" is an amount of the compound of the invention, or a composition containing the compound, where 25% or greater mortality against pests is achieved, preferably 50% or greater, more preferably 70% or greater mortality. Similarly, an "effective pest-growth modulating amount" is preferably one where 25% or greater pest-growth modulation is achieved, preferably 50% or greater, more preferably 70% of greater. The term "amount sufficient to prevent infestation" is also used herein and is intended to mean an amount that is sufficient to deter all but an insignificant sized pest population so that a disease or infected state is prevented.

The actual value of a pesticidally effective amount for a given compound is preferably determined by routine screening procedures employed to evaluate pesticidal activity and efficacy, such as are well known by those skilled in the art and as are described in the Examples. It is expected that compounds of the invention having a higher level of pesticidal activity can be used in smaller amounts and concentrations, while those having a lower level of activity may require larger amounts or concentrations in order to achieve the same pesticidal effect. Efficacy is also monitored by phytotoxicity to the plants that are infested with the pest population, tissue damage to the host infected with the pest population and any adverse effects that might be experienced by a human user who is applying the composition to an infested plant or animal. Accordingly, the amount of composition or active compound used in the methods of the invention, meets the mortality, modulation or prevention criteria above, and preferably has minimal or no adverse effect on ornamental and agricultural plants (such as phytotoxicity), wildlife and humans that may come into contact with such compound.

The compounds of the invention have pesticidal activity against one or more pests. However, it is understood that certain compounds may be more effective on some pests than others, and may even be ineffective against some pests. However, that does not in any way detract from their value as pesticides since the invention contemplates using some of these compounds as broad, general acting pesticides, while others have utility as specific or selective pesticides. The Examples set forth below illustrate methods by which the broad-acting or selectivity of pesticidal activity may be readily ascertained.

The compounds useful in this invention are represented by Formula (I) and (II):

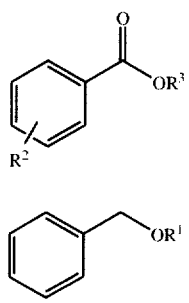

(I)

(II)

wherein $R^1$ is alkylcarbonyl, preferably $C_{1-5}$alkylcarbonyl; $R^2$ is H, OH, halogen, alkyl, preferably $C_{1-6}$alkyl, alkoxy, preferably $C_{1-6}$alkoxy or —COOR$^4$, where $R^4$ is alkyl, preferably $C_{1-6}$alkyl, or H; and $R^3$ is alkyl, preferably $C_{1-6}$alkyl, aryl or arylalkyl, preferably aryl$C_{1-6}$alkyl such as benzyl.

As used herein the term "alkyl" means a branched or unbranched saturated monovalent hydrocarbon radical containing 1 to 12 carbon atoms, such as methyl, ethyl, propyl, isopropyl, tert-butyl, butyl, n-hexyl, dodecyl, and the like, unless otherwise indicated. Preferably the alkyl group is a lower alkyl (branched or unbranched saturated monovalent hydrocarbon radical) having 1 to 6 carbon atoms ($C_{1-6}$), such as methyl, ethyl, tert-butyl, and the like.

"Alkoxy" means the group alkyl-O— wherein alkyl is as herein defined. Preferably the alkoxy group has 1 to 4 carbon atoms ($C_{1-4}$).

"Arylalkyl" refers to a monovalent unsaturated aromatic carbocyclic radical having a single ring (e.g., phenyl) attached through an alkyl group, which preferably has 1 to 6 carbon atoms ($C_{1-6}$), i.e., aryl$C_{1-6}$alkyl. More preferably the arylalkyl group is an aromatic ring attached through a —CH$_2$-group (e.g., benzyl).

"Alkylcarbonyl" refers to an alkyl group attached through a carbonyl, —C(O)— group, and includes by way of example, methyl carbonyl and ethyl carbonyl. Preferably the alkylcarbonyl group is a $C_{1-5}$alkylcarbonyl carbonyl group.

Compounds of particular interest include those listed in Tables I and II below, where the "R" groups correspond to the "R" groups defined for Formulas (I) and (II). It is to be understood that the compounds shown are merely representative and not exhaustive. Others will be apparent to those of skill in the art, given this disclosure.

TABLE I

| Formula (I) Compounds | | | |
|---|---|---|---|
| Name | $R^2$ | $R^4$ | $R^3$ |
| methyl salicylate | —OH | — | Me |
| ethyl salicylate | —OH | — | Et |
| benzyl salicylate | —OH | — | Bz |
| benzyl benzoate | H | — | Bz |
| phenethyl salicylate | —OH | — | —Et—Ph |
| phenyl salicylate | —OH | — | Ph |
| benzyl phthalate | —COOR$^4$ | H | Bz |
| benzyl butyl phthalate | —COOR$^4$ | Bu | Bz |

TABLE II

| Formula (II) Compounds | |
|---|---|
| Name | $R^1$ |
| benzyl acetate | $CH_3$—C(O)— |

The following abbreviations are used in Tables I and II: "Et" is ethyl, "Me" is methyl, "Bu" is butyl, "Ph" is phenyl and "Bz" is benzyl.

Compounds useful in the composition of this invention are available from commercial sources known in the art, such as Aldrich Chemical Co., Sigma Chemical Co., or are readily synthesized by techniques as are well known in the art. For example, benzyl benzoate, benzyl salicylate and benzyl acetate can be obtained from B. F. Goodrich/Kalama Chemical Inc. (Kalama, Wash.) and Pentagon Chemical (Los Angeles, Calif.).

Benzyl benzoate, (CAS Registration number 120-51-4), is widely used in the perfume and pharmaceutical industries. Its high molecular weight and nearly odorless nature make it a widely used perfume fixative. Benzyl benzoate has application in confectioneries and chewing gums and is produced commercially to meet the specifications described in the United States Pharmacopoeia (USP) and the Food Chemicals Codes (FCC). Benzyl benzoate is found as a natural chemical in the volatile oil of the *Myroxylon pereirae* (Royle) Klotzch of the Family Leguminosae or Fabaceae. Benzyl benzoate also is found in the balsams of Tolu and Peru and in the oils of tuberose, ylang-ylang, and hyacinth. Benzyl benzoate can be synthesized via the Cannizarro reaction from benzyl chloride and sodium benzoate. Benzyl salicylate, (CAS Registration number 118-58-1), is a natural product of *Dianthus caryophyllus* L. Benzyl salicylate can be prepared by sodium salicylate and benzyl chloride (*J. Am. Chem. Soc.* (1921) 43:1672), and is readily available from commercial sources such as B. F. Goodrich/Kalama Chemical. Benzyl acetate occurs in a number of plants, particularly jasmine. Benzyl acetate can be prepared from benzyl chloride, acetic acid or sodium acetate and triethylamine (*J. Org. Chem.* (1961) 26:5180). Benzyl phthalate can be prepared from disodium phthalate and benzyl chloride (U.S. Pat. No. 3,012,065). The $LD_{50}$s on rats of benzyl benzoate, benzyl salicylate and benzyl acetate are 1,830; 2,227; and 2,490 mg/Kg, respectively, (Merck Index); higher than those of many currently used pesticides.

Referring to Formula (I), the preferred $R^2$ substituent is H, —OH or —COOR$^4$, where $R^4$ is $C_{1-6}$alky. $R^2$ is more preferably H, —OH or —COO—(CH$_2$)$_3$CH$_3$. The preferred $R^3$ substituent is $C_{1-6}$alkyl, phenyl or aryl$C_{1-6}$alkyl such as benzyl. $R^3$ is more preferably methyl, ethyl, benzyl or phenyl.

Preferred compounds of Formula (I) include methyl salicylate, ethyl salicylate, benzyl salicylate, benzyl benzoate, phenethyl salicylate, phenyl salicylate, benzyl phthalate and benzyl butyl phthalate. Even more preferred compounds of Formula (I) include methyl salicylate, ethyl salicylate, benzyl salicylate, benzyl benzoate, phenyl salicylate and benzyl butyl phthalate. Particularly preferred compounds of Formula (I) include ethyl salicylate, benzyl salicylate and benzyl benzoate.

Referring now to Formula (II), the preferred the preferred $R^1$ substituent is alkylcarbonyl, preferably $C_{1-5}$alkylcarbonyl, more preferably methylcarbonyl. A particularly preferred compound of Formula (II) is benzyl acetate.

The subject composition offers several advantages over currently used pesticides. First, the preferred compounds used in the composition of the invention are naturally-occurring compounds, and as such are expected to generally exhibit a very high $LD_{50}$ against animals and thus are relatively nontoxic to humans, domestic animals and wildlife. Consequently, when used for treating plant pests, food crops can be treated using the composition up to and immediately before the harvesting period, a practice that generally is avoided when using conventional methods of pest control. The composition also can be used to control the growth of pest organisms on harvested crops. The harvested food can be used directly as food for animals or humans with little fear of residual toxicity. By using the subject compositions, the environmental and health hazards involved in pest control are minimized by reducing the toxicity of the chemical compounds. Because of the low toxicity, when necessary, the composition can be used as a preventative on a repeated basis and, thus, can be integrated into integrated pest management (IPM) programs. The composition can be applied to skin or to objects such as clothing, fur, feathers, or hair which come into contact with skin when used to treat pests that infest animals. The active compound, i.e., the active ingredient, of the pesticides of the present invention are believed to be biorational chemicals that qualify for the US EPA Biorational Program.

Another advantage of the composition is that the compounds used have not previously been used as a pesticide against microorganisms, and therefore, fungal and bacterial pathogens and other pest organisms have not acquired resistance to them. Disease resistance to chemicals other than the heavy metals occurs commonly in pests such as fungi and on rare occasions in bacterial plant disease pests. A new pesticide often becomes noticeably less effective against a particular disease after several growing seasons. As pesticides become more specific for diseases, the pests become resistant. This can be attributed to the singular mode of action of a particular pesticide, which disrupts only one genetically controlled process in the metabolism of the pest organism. The result is that resistant populations appear suddenly, either by selection of resistant individuals in a population or by a single gene mutation. Generally, the more specific the site and mode of a pesticidal action, the greater the likelihood for a pest organism to develop a tolerance to that chemical. A new composition will solve the disease resistance problem. To avoid developing future disease resistance in pests, different chemicals should be alternated for treatment with the methods of the invention.

The subject methods offer several advantages over existing methods of pest control. The formulations of the subject invention provide for effective control of both microorganisms such as fungi and insects, eliminating the need for application of multiple agents. In particular situations, such as where an insect damages a plant part or tissue and a secondary fungal disease develops, this aspect of the invention is particularly advantageous. The long term control of pests results in a healthier plant and an improved quality and yield of produce by the host plant as compared with untreated plants. The low concentration and single dose of anti-pest agents decreases the likelihood of damage to the plant and/or its crop, and decreases the likelihood of adverse side effects to workers applying the pesticide, or to animals, fish or fowl which ingest the tissues or parts of treated plants.

The composition may be solid (i.e., in a powdered form) or liquid depending on the carrier and the needs of the user. If the composition is solid, suitable carriers include various known, agriculturally-useful powders that are generally used for this purpose. If the composition is liquid, it may be aqueous or non-aqueous and may be a solution, suspension, or emulsion, depending on the needs of the user applying the pesticidal composition.

Generally, a composition of this invention will be prepared as a concentrate for industrial application and further dilution or as a fully diluted ready-to-apply composition. Preferably, the composition is applied as a liquid, whether aqueous or non-aqueous, but preferably the former. The concentrate, if solid, will be formulated to be mixed to form an appropriate non-aqueous or aqueous composition. Thus, the composition will generally contain the active compound along with a surfactant carrier to effect miscibility or suspendability of the composition in a liquid.

The composition of the invention is either non-phytotoxic or non-dermal sensitive if the intended application is to the tissue of a plant or animal host, respectively. The preferred compositions comprise a pesticidally active compound of the invention, present in a pesticidally effective amount. In general, the percentage by weight of the active compound, i.e., the active ingredient will be about 0.1% to 50 wt %. The preferred amount is determined using bioassays on a pest-by-pest basis. The higher concentrations are usually preferred for purposes of manufacture, shipment, and storage. For example, as a concentrate for use by professional agronomists the percentage will be at least about 10 wt %, preferably about 25 to 50% by weight. Prior to use, the high concentration composition is diluted in a solvent to an appropriate concentration for the intended use of the composition. When fully diluted for consumer use as a "ready for use" product, the composition will be typically be about 0.5% to 10 wt %, more preferably 1 to 5 wt %.

The subject composition can include an antioxidant at a level sufficient to increase the product shelf life, inhibit decomposition of the active compound in the herbicidal composition, or improve the stability of the controlling effect when the composition is applied to hosts infested with the targeted pests. Suitable antioxidants, include, but are not limited to, ascorbyl palmitate, anoxomer, benzoic acid, benzlkonium chloride, benzethonium chloride, benzyl alcohol, butylated hydroxyanisole, butylated hydroxytoluene, chlorobutanol, dehydroacetic acid, ethylenediamine, ferulic acid, potassium benzoate, potassium metabisulfite, potassium sorbate, n-propyl gallate BP, propylparaben, sassafras oil, sodium benzoate, sodium bisulfite, sodium metabisulfite, sorbic acid, vitamin E, eugenol, α-tocopherol, and the like. Particularly suitable antioxidants include sodium benzoate, vitamin E and α-tocopherol. Antioxidants can be included in the composition so long as the formulation remains biologically compatible if applied to a host. The amount of antioxidant used is in general about 0.01–10% by weight, but generally no more than about 1 wt %. A preferred amount can be determined by a shelf-life stability trial in accordance with an EPA standard protocol. A minimal amount of antioxidant which increases shelf life and/or maintains product stability is selected to reduce manufacturing costs.

The subject composition can be an aqueous composition using water solvent or an organic composition using an organic solvent, such as ether, ketone, kerosene, or alcohol where the application is not directly to a host tissue, or in a concentration of organic solvent that will not harm a host tissue if applied to a host tissue. A water solvent is preferred because it mimics nature (biorational), is environmentally safe, is non-phytotoxic or non-dermal sensitive, and also costs little. The compositions of this invention, particularly liquids and soluble powders, preferably contain, as a conditioning agent, one or more surface-active agents in amounts sufficient to render a given composition readily dispersible in water or in an organic solvent. The incorporation of a surfactant into the compositions greatly enhances their efficiency. The water, organic solvent, or surfactant (alone or in combination with a solvent) functions as the agriculturally-acceptable carrier.

By the term "surfactant" it is understood that wetting agents, dispersing agents, suspending agents, and emulsifying agents are included therein. Anionic, cationic and non-ionic agents can be used, although non-ionic agents are preferred. The non-ionic surface-active agents include allinol, nonoxynol, octoxynol, oxycastrol, oxysorbic (for example, polyoxyethylated sorbitol fatty-acid esters (TWEEN®)); thalestol, and polyethylene glycol octylphenol ether (TRITON®). The anionic type of agents include fatty-acid salts, higher alcohol sulfuric esters and alkylallylsulfonates; the cationic type of agents include aliphatic amino salts, quaternary ammonium salts and alkylpyridinium salts, individually or in combination. Particularly suitable surfactants include, by way of illustration and not limitation, TWEEN®20 (polyoxyethylene sorbitan monolaurate), TWEEN®40, TWEEN®80, along with TRITON®SP150, TRITON®SP180 and TRITON®SP190; the most preferred being TWEEN®80 and TRITON®SP190. Of these, the nonionic surfactants are preferred. Usually, the amount of surfactant used is the minimum amount required to get the compound into solution/emulsion, and will generally be 0.5 to 10% by weight, more typically 0.5 to 1%.

The common and chemical names of other generally available adjuvants include, but are not limited to, the following list, in which the first name is the common name used in the industry, the second name is the general chemical name, the third name is the class of the compound, the fourth name is the type of surfactant, and the trade name is last.

Albenate: Alkyl($C_{18}C_{24}$)benzene sulfonic acid and its salts; Alkylaryl sulfonate; Anionic surfactant; Nacconol 88SA, Calsoft F-90, DDBSA, Santomerse No. 3.

Alfos: $\alpha$-Alkyl($C_{10}$–$C_{16}$)-$\omega$-hydroxypoly(oxyethylene) mixture of dihydrogen phosphates esters; polyoxyethylene alkyl phosphate ester; Anionic; Emcol PS-131.

Allinate: $\alpha$-Lauryl-$\omega$-hydroxypoly(oxyethylene) sulfate; lauryl polyoxyethylene sulfate salts; Anionic; Sipon ES.

Allinol: $\alpha$-Alkyl($C_{11}$–$C_{15}$)-$\omega$-hydroxypoly(oxyethylene); $C_{11}C_{15}$ linear primary alcohol ethoxylate; Nonionic; Neodol 25-3, Alfonic 1014-40 and other alfonic materials.

Diocusate: Sodium dioctyl-sulfosuccinate; Dioctyl sodium sulfosuccinate; Anionic; TRITON GR-5, Aerosol OT.

Dooxynol: $\alpha$-(p-Dodecyl-phenyl)-$\omega$-hydroxypoly(oxyethylene); dodecylphenol condensation with ethylene oxide; Nonionic; Igepal RC-630, Tergitol 12-P-9, Sterox D Series.

Ligsolate: Lignosulfonate, $NH_4$, Ca, Mg, K, Na, and Zn salts; Salts of lignosulfonic acids; Anionic; Marasperse N-22, Polyfon O.

Nofenate: $\alpha$-(p-Nonylphenyl)-$\omega$-hydroxypoly(oxyethelene) sulfate, $NH_4$, Ca, Mg, K, Na, Zn salts, Nonyl group is a propylene trimer isomer; Salts of sulfate ester of nonylphynoxypoly(ethyleneoxy) ethanol; Anionic; Alipal CO Series Nonfoster: $\alpha$-(p-Nonylphenyl)-$\omega$-hydroxypoly(oxyethylene); mixture of dihydrogen phosphate and nonophosphate esters; Polyoxyethylene nonylphenol phosphate esters; Anionic; Gafac RM 510.

Nonoxynol: $\alpha$-(p-Nonylphenyl)-$\omega$-hydroxypoly(oxyethylene); polyoxyalkylene nonylphenol; Nonionic; Sterox N Series, Makon 6, Igepal CO Series TRITON N Series, T-DET N.

Octoxynol: $\alpha$-[p-1,1,3,3-Tetramethyl butyl phenyl]-$\omega$-hydroxypoly(oxyethylene); polyoxyethylene octyl phenol; Nonionic; Igepal CA-630, TRITON X-100.

Oxycastol: Castor oil polyoxyethylated; Ethoxylated castor oil; Nonionic; Emulphor EL-719, Emulphor EL-620, Trylox CO-40, T-DET C-40

Oxysorbic: Polyoxyethylated sorbitol fatty acid esters (nonosterate, monoleate etc.); Polyoxyethylated sorbitol fatty acid esters; Nonionic; Atlox 1045, Drewmulse POESTS, TWEEN Series G-1045.

Tall oil: Tall oil, fatty acids not less than 58%, rosin acids not greater than 44%, unsapolifiables not greater than 8%; Tall oil; Anionic; Ariz. S.A. Agent 305.

Thalestol: Polyglyceryl phthalate ester of coconut oil fatty acid; Modified phthalic glycerol alkyl resin; Nonionic; TRITON B-1956.

The composition can include other active or inactive substances. In some instances, the efficacy of the formulation can be increased by adding one or more other components to the formulation. It is preferable that the additional component(s) minimize toxicity to hosts such as plants or mammals while increasing the anti-pest effect of the formulation. Especially preferred is the use of a synergist, which is a component that, by virtue of its presence, increases the desired effect by more than an additive amount. Of particular interest is the addition of components to a formulation to allow for a reduction in the concentration of one or more active compounds, i.e., the active compound(s) in a given formulation while substantially maintaining efficacy of the formulation.

The subject composition may be prepared by simply mixing together the requisite amount of at least one compound of the invention and at least one agriculturally acceptable carrier, i.e., surfactant, alone or with a solvent. Other additives, such as saponins and antioxidants, may be included prior to mixing.

The composition can be encapsulated or microencapsulated; it can also be produced as dust, powder, etc. A preferred pH of the composition is between 6.0 and 8.0 with an optimal range of 6.5–7.5. A neutralized composition is preferred to lower the risk of harm caused by alkalinity. Water-dispersible powder, capsule, or pellet compositions can be made containing one or more compounds of the invention, an inert solid extender, and one or more wetting and dispersing agents. The inert solid extenders are usually of mineral origin, such as natural clays, diatomaceous earth and synthetic minerals derived from silica and the like. Examples of such extenders include kaolinites, attapulgite clay and synthetic magnesium silicate. The water-dispersible powders can also include fatty-acid esters and antioxidants.

For controlling the growth of pests on a plant or a plant part (such as foliage/leaves, trunk, stems, branches or roots and so forth), the method of the invention can be carried out by applying a pesticidally effective amount of the subject composition to a plant host or to the substrate in which it is growing or is to be grown. For controlling pests on other than a plant or a plant part, a method is provided to obtain and/or maintain an area substantially free of pests, using the subject compositions. The pests are controlled via either direct pesticidal activity on a target pest or via indirect pesticidal activity by anti-bacterial action on symbiotant bacteria resident in the target pest. The composition is provided to pests to eliminate them, to deter their growth, and/or to prevent infestation of a host for the pests. The method of introduction of the subject pesticide into the target pest can be by contacting the pest, by direct ingestion by the target pest from a trap, or by feeding a target pest on nutrient-providing, organic matter treated with the pesticide. In some instances, the pesticide is absorbed by the pest, particularly where the formulation, for example, a detergent formulation, provides for uptake by the outer tissues of the pest, particularly a larval or other pre-adult form of the pest. In some instances, the exoskeleton of the target pest is substantially dissolved by contact with the formulation. For some applications, it may be necessary to deliver the formulation to the location of the pest colony.

The method of use of the compounds and compositions of the invention will depend at least in part upon the pest to be treated and its feeding habits, as well as breeding and nesting habits. While very minor dosage rates of the novel compositions will have an adverse effect on pests, adequate control usually involves the application of a sufficient amount to either eliminate pests entirely or significantly deter their growth and/or rate of proliferation. Dosage rates required to accomplish these effects, of course, vary depending on the target pest, size, and maturity, i.e., stage of growth. More mature pests are generally more resistant to pesticides and require higher dosage rates for a comparable level of control. Dose response experiments using different dilutions (for example, 1:1000, 1:100, 1:10 and 1:3) of the pesticidally active compound on target organisms and on plants are performed to determine the optimal concentration of the active compound that shows a biopesticidal activity without phytotoxicity or dermal sensitivity.

Infestation of target pests can be treated with a solid support associated with the composition such as a bait or a trap, or treated with powder or detergent formulations. The composition also can be sprayed on as a wet or dry composition on the surface of material infested with a target pest, or material susceptible to infestation with a target pest. Alternately, the composition can be applied wet or dry to an area of infestation where it can contact the target pest.

The composition can be used as a fumigant to mix with pre-plant soil for crops such as tomatoes, strawberries, cucumbers, watermelons and pumpkins, to kill nematodes, insects, weed seeds, fungi and soil-born pathogen. The composition also can be used as insect/rodent fumigant for storage and transportation of agricultural produce. The amount of anti-pathogenic agent that is applied either to the plant itself or to the rhizosphere will depend upon the degree of infestation and to some extent, upon the formulation of the composition used, and therefore is empirically determined for best results.

When the area of infestation is a plant or a plant part, a composition containing the pesticidally active compound of the invention is provided to a plant tissue or a plant part either pre- or post-harvest of the plant or plant part. Methods of application include spraying, pouring, dipping, injecting, fogging, fumigation or the like, along with applying the composition by means of power dusters, boom and hand sprayers and spray dusters. The compositions can also be applied from airplanes as a dust or a spray because of their effectiveness at low dosages. The active compound can be in the form of a concentrated liquid, solution, suspension, powder or the like. For example, the composition can be sprayed on as a wet or dry composition to the surface and/or underside of the leaves or other plant tissue or part of a plant infected with a plant pathogen, or of a plant susceptible to infestation with a plant pathogen, preferably to the point of run off when a wet formulation is used. The plants can be sprayed prior to or after infestation, preferably prior to infestation. However, in order to minimize damage to the host plant, where feasible, it is preferable to treat older plants, as young green leaves tend to be more sensitive to phytotoxicity. The formulation also can be applied wet or dry, either as part of an irrigation schedule or as a separate application, to the rhizosphere where it can contact the roots of the plant and associated pathogenic organisms which colonize the roots. In some instances, time-release formulations may find use, particularly for applications to the rhizosphere, or to post harvest materials.

For controlling the growth of pathogenic organisms on a plant or a plant part, a composition comprising a pesticidally effective amount of the compounds described herein is applied to the plant or plant part. The composition is provided in a non-phytotoxic solvent to minimize damaging the plant. The phytotoxicity of the formulation can be evaluated by applying the composition on living plants and determining the toxicity of the composition to the plants. As stated above, a non-organic aqueous solvent or emulsion is in general preferable for its non-phytotoxicity, and a fatty-acid ester is sometimes included in the formulation to increase the pesticidal activity of the formulation, thus reducing the necessary amount of the active compounds. The efficacy of treatment is monitored by determining the mortality of pathogens and phytotoxicity; absence of phytotoxicity and 70% or greater mortality against insects, athropods, bacteria and fungi are desirable.

Plants suitable for treatment are those of agricultural and/or horticultural importance, such as food crops, fruit trees and ornamental plants and flowers. These include by way of illustration and not limitation, fruit bearing plants and trees including grape vines, strawberry plants, apple, pear, citrus and other fruit trees, tomato plants, cucumbers, lettuce varietals; ornamental plants and trees such as roses and miniroses, carnations, tulips, herbs, rhododendron, magnolia, primroses, orchids, chrysanthemums and poinsettias; and other agricultural crops such as cotton.

It is also expected that the methods described herein can employ the compositions of this invention, along with sequential treatments with herbicides, phytotoxicants, fertilizers, and the like for maximum effect. For example, a field could be sprayed with a composition of this invention either before or after being treated with fertilizers, herbicides, phytotoxicants, and the like. The compositions of this invention can also be admixed with other materials, e.g., fertilizers, herbicides, phytotoxicants, etc., and can be applied in a single application.

For controlling pathogenic organisms on areas other than a plant or a plant part, a formulation comprising a pesticidally effective amount of a compound of the invention is applied to the area infested or subject to infestation by pathogenic organisms. As appropriate, for example, when the composition is to be applied to the skin of a mammal or to objects or materials which can come into contact with the skin of a mammal, the composition is evaluated for dermatological effects. It is important where appropriate that at least one evaluation of the toxicity of the composition be tested on animal hosts for the target pest or on animals which may come in contact with a treated surface so that the dermatological effects can be evaluated for the dosage of pesticide used. Such dermatological sensitivity tests can be conducted using methods known to those skilled in the art (see Kligman (1966) *J. Invest. Dermatol.*, 47:393). In some instances it may be necessary to adjust the treatment composition so as to reduce any dermatological effects associated with the formulation of the composition. When applied to animals, including humans, the subject composition is provided in a carrier which is non-toxic- and non-irritating to the skin. Animals to be treated include humans, companion animals (e.g., feline and canine), and agriculturally bred animals, including those raised for human consumption, such as bovine and poultry (e.g. avian).

One application of the composition of the invention is generally enough, but more than one application may be made to obtain the desired results. In a preferred embodiment of the invention, the method involves a single treatment of the composition described herein, which provides not only long lasting protection against pests, but also often is effective at a site on the plant remote from the point at which the subject formulations are applied. For example, foliar application of the subject composition is effective against pathogens that colonize relatively remote and inaccessible regions of the plant, such as the roots and the meristems. It is a theory of this invention that this remote effect occurs because the subject composition is transported in the plant vascular system, which allows for long distance transportation of the compounds within living plants, and/or because application of the subject formulations induces systemic-acquired resistance.

These methods are best illustrated by the preferred embodiments set forth below. One aspect of this invention is a method of controlling pests, for example by eliminating or deterring the growth of the pest population, which involves applying a composition of this invention to a pest or a site of pest infestation (such as a plant, plant part, or animal) at a pesticidally effective level. As noted above, application methods include ground, aerial, chemigation, surface, soil incorporation, preplant, preemergent, postemergent, spraying, brushing, dipping, and the like, depending on the conditions of the weather, the type of pest, the type of plant or animal being treated, the time of year, and other factors known to those of skill in the art.

An exemplary method for controlling pests comprises applying (such as by spraying) to a pest or site of pest infestation, a pesticidally effective amount of a composition comprising an agriculturally-acceptable carrier in combination with a compound of Formula (I) or (II). Preferably, the composition is applied in an amount sufficient to prevent infestation of the host and the composition does not damage the host's tissue. Of particular interest is use of the pesticide compositions of the invention in treating fungal infestations of fruit bearing plants such as strawberry plants. By treatment of a diseased plant with the composition of the invention in an amount sufficient to treat such a fungal infestation, pests such as powdery mildew can be controlled or eliminated, thus restoring the plant to a healthy state. Also of particular interest is use of the pesticide compositions of the invention in controlling arthropod infestations of ornamental plants such as roses. By treatment of a diseased plant with the composition of the invention in an amount sufficient to treat such a arthropod infestation, pests such as aphids and spider mites can be controlled or eliminated, thus restoring the plant to a healthy state.

Use of pesticides is regulated in the United States by the Environmental Protection Agency (EPA) under authority of the Federal Insecticide, Fungicide and Rodenticide Act (FIFRA). Tolerance for residues of pesticides in agricultural commodities are established by the (EPA) and enforced by the Food and Drug Administration (FDA) under authority of the Federal Food, Drug and Cosmetic Act (FD&C Act).

This regulatory environment leads to another aspect of this invention, which is an article of manufacture. In this aspect a pesticidally active compound represented by Formula (I) or (II), as defined above, is combined with an agriculturally-acceptable carrier in a container that will be suitable for storing the composition for its shelf life. Associated with the container is printed instructions and/or a printed label indicating that the subject composition can be used to control pests, i.e., used as a pesticide and providing instructions for using the composition for pesticidal purposes in accordance with the treatment method set forth herein. The container may have associated with it a delivery device that allows the composition to be applied to the pest population or to the area to be treated. For liquid compositions this is generally a hand-operated, motorized or pressurized pressure-driven sprayer. The container may be made of any suitable material such as a polymer, glass, metal, or the like. Usually, the labeling is associated with the container by being adhered to the container, or accompanying the container in a package sold to the user. Such label may indicate that the composition is approved for use as a pesticide. The instructions will spell out the type of pests for which the pesticidal composition is to be used, the application method, the rate of application, dilution requirements, use precautions, and the like.

The following examples are presented as illustrations, not limitations.

EXAMPLES

Abbreviations

| | |
|---|---|
| BB | Benzyl Benzoate |
| BS | Benzyl Salicylate |
| ES | Ethyl Salicylate |
| T20 | TWEEN ® 20 |
| T80 | TWEEN ® 80 |

Example 1

Insecticidal Properties of Benzyl Benzoate on Melon Aphids

A formulation of 2.5% BB, 0.1% T80 and a water only control, were applied to melon aphids infested chrysanthemums in three replicated experiments. Both pest and control formulation were applied via direct contact spray on foliage to runoff. The dead and live insects were counted after 24 hours. The results are summarized in Table III. The results demonstrated that the benzoate formulation had clear efficacy against melon aphids with no phytotoxicity to chrysanthemums.

TABLE III

| | Mortality of Aphids | | | |
|---|---|---|---|---|
| | Rep. 1 dead:live (#) | Rep. 2 dead:live (#) | Rep. 3 dead:live (#) | Total Mortality (%) |
| 2.5% BB, 0.1% T80 | 65:11 | 14:0 | 42:2 | 90.3 |
| Control (H$_2$O) | 3:22 | 14:90 | 7:51 | 12.8 |

Example 2

Insecticidal Properties of Benzyl Benzoate and on Melon Aphids

A formulation of 1.5% BB, 0.5% T80 and a water only control were applied to melon aphids infested chrysanthemums in three replicated experiments. Both pest and control formulations were applied via direct contact spray on foliage to runoff. The dead and live insects were counted after 24 hours. The results are summarized in Table IV. None of the treatments resulted in phytotoxicity of chrysanthemums. The BB/T80 treatment killed the aphids in their tracks; the aphids did not desiccate, instead appeared preserved.

TABLE IV

Mortality of Melon Aphids

|  | Rep. 1 dead:live (#) | Rep. 2 dead:live (#) | Rep. 3 dead:live (#) | Total Mortality (%) |
|---|---|---|---|---|
| 1.5% BB, 0.5% T80 | 268:20 | 243:40 | — | 89.4 |
| Control (H₂O) | 0:207 | 0:312 | — | 0 |

Example 3

Insecticidal Properties of Benzyl Benzoate on Thrips

A formulation of 1.0% BB, 0.1% T80 and a water only control were applied to Western flower thrips (larvae and pupae) on rose. Both formulations were applied via direct contact spray. The results are summarized in Table V. The results show that the test formulation had clear efficacy against Western flower thrips, and the formulation does not cause phytotoxicity to roses.

TABLE V

Mortality of Western Flower Thrips

|  | Rep. 1 dead:live (#) | Rep. 2 dead:live (#) | Rep. 3 dead:live (#) | Total Mortality (%) |
|---|---|---|---|---|
| 1.0% BB, 0.1% T80 | 7:0 | 11:3 | 6:1 | 85.7 |
| Control (H₂O) | 0:6 | 0:5 | 1:9 | 0.5 |

Example 4

Insecticidal Properties of Benzyl Benzoate on Melon Aphids

A formulation of 1.5% BB, 0.3% T80 and a formulation of 0.3% T80 were applied to melon aphids. Both formulations were applied via direct contact spray. The treatment results of melon aphids on chrysanthemum are summarized in Table VI. The results show that BB had clear efficacy against melon aphids. The phytotoxicity of plants were also observed. Chrysanthemum showed no phytotoxicity for 5 days, only the lowest leaves showed two necrotic spots but no serious damage. Minirose, magnolia and primrose showed no damage or stress, with treatments, when observed at 7 and 12 days.

TABLE VI

Mortality of Melon Aphids

|  | Rep. 1 dead:live (#) | Rep. 2 dead:live (#) | Rep. 3 dead:live (#) | Total Mortality (%) |
|---|---|---|---|---|
| 1.5% BB, 0.3% T80 | 33:4 | 59:11 | 44:9 | 85 |

TABLE VI-continued

Mortality of Melon Aphids

|  | Rep. 1 dead:live (#) | Rep. 2 dead:live (#) | Rep. 3 dead:live (#) | Total Mortality (%) |
|---|---|---|---|---|
| Control (0.3% T80) | 0:76 | 2:56 | 3:69 | 2.4 |

Example 5

The Miticidal Properties of Benzyl Benzoate

A formulation of 2.5% BB, 0.1% T80 and a water only control were applied to two-spotted spider mites on roses. Both were applied via direct contact spray. The results are summarized in Table VII. The results clearly indicate efficacy of the BB formulation against two spotted spider mites. There was no phytotoxicity observed on the roses.

TABLE VII

Mortality of Two-Spotted Mite

|  | Rep. 1 dead:live (#) | Rep. 2 dead:live (#) | Rep. 3 dead:live (#) | Total Mortality (%) |
|---|---|---|---|---|
| 2.5% BB, 0.1% T80 | 127:21 | 83:4 | 91:9 | 90.0 |
| Control (H₂O) | 22:90 | 7:63 | 2:107 | 10.6 |

Example 6

The Miticidal Properties of Benzyl Benzoate

A formulation of 1.0% BB, 0.1% T80 and a water only control were applied to two-spotted spider mites on roses. Both formulations were applied via direct contact spray. The results are summarized in Table VIII. The results indicate efficacy of the benzyl benzoate formulation against two-spotted spider mites with no phytotoxicity to roses.

TABLE VIII

Mortality of Two-Spotted Spider Mite

|  | Rep. 1 dead:live (#) | Rep. 2 dead:live (#) | Rep. 3 dead:live (#) | Total Mortality (%) |
|---|---|---|---|---|
| 1.0% BB, 0.1% T80 | 60:11 | 87:14 | 132:22 | 85.6 |
| Control (H₂O) | 12:77 | 7:81 | 17:117 | 11.6 |

Example 7

The Insecticidal and Miticidal Properties of Benzyl Salicylate

A formulation of 1.0% BS, 0.2% T20 and a 0.2% T20 control formulation were applied to melon aphids and two-spotted spider mites on minirose, magnolia, chrysanthemum and primrose. Both formulations were applied via direct contact spray. The results of melon aphids on minirose are summarized Table IX. The results of two-spider spots on minirose are summarized in Table X. The results clearly indicate the efficacy of BS against melon aphids and two-spotted spider mites. The phytotoxicity of the formulation on the plants was also observed. Minirose, magnolia and primrose, showed no damage and no stress with the treatments, when observed at 7 days. Chrysanthemums showed severe damage from leaf tips moving inwards, and some leaf damage beginning from bottom leaves and moving upwards, with the newest leaves remaining unaffected, when observed at 7 days.

TABLE IX

Mortality of Melon Aphids

|  | Rep. 1 dead:live (#) | Rep. 2 dead:live (#) | Rep. 3 dead:live (#) | Total Mortality (%) |
|---|---|---|---|---|
| 1.0% BS, 0.2% T20 | 27:2 | 36:7 | 12:0 | 89.3 |
| Control (0.2% T20) | 6:38 | 3:52 | 12:33 | 14.7 |

TABLE X

Mortality of Two-Spotted Mite

|  | Rep. 1 dead:live (#) | Rep. 2 dead:live (#) | Rep. 3 dead:live (#) | Total Mortality (%) |
|---|---|---|---|---|
| 1.0% BS, 0.2% T20 | 47:3 | 20:1 | 92:20 | 86.9 |
| Control (0.2% T20) | 6:77 | 2:19 | 2:44 | 6.7 |

The above examples demonstrate that a benzyl benzoate composition is effective for controlling aphids, thrips, and spider mites; and benzyl salicylate is effective in controlling aphids and spider mites. Minirose, magnolia and primrose showed no phytotoxicity from the treatments of the benzyl benzoate and benzyl salicylate compositions. Chrysanthemums showed no phytotoxicity by the treatment with benzyl benzoate.

Example 8

Summary Results

TABLE XI

Pesticidal Efficacy

| Active Compound | benzyl salicylate | benzyl acetate | benzyl benzoate | ethyl salicylate | methyl salicylate | benzyl butyl phthalate | phenyl salicylate |
|---|---|---|---|---|---|---|---|
| Pest: |  |  |  |  |  |  |  |
| melon aphid | 98/1.0 | 90+/5.0 | 74/1.0 | 90/5.0 | 90/5.0 | 70/5.0 | 90/5.0 |
| silverleaf whiteflies | 70/0.5 | — | 39/1.0 | — | — | — | — |
| leafminer | 25/1.0 | — | 24/2.0 | — | — | — | — |
| western flower thrips | 36/0.5 | — | 14/0.25 | — | — | — | — |
| honey bee | 78/1.0 | — | 68/0.3 | — | — | — | — |
| two-spotted spider mite | — | 90+/5.0 | — | 90/5.0 | 90/5.0 | 50/5.0 | 90/5.0 |
| Argentine ant | 99/1.0 | — | — | — | — | — | — |
| pharaoh ant | 89/5.0 | — | 21/5.0 | — | — | — | — |
| American cockroach | — | — | — | 100/5.0 | — | — | — |
| German cockroach | 0/1.1 | — | 0/1.0 | — | — | — | — |
| cat flea | 100/5.0 | — | 93/5.0 | — | — | — | — |
| housefly | 47/0.1 | — | 35/0.1 | — | — | — | — |

The first number indicates the highest observed mortality (%) and the second number indicates the concentration of the AC (by weight %) in the formulation tested. For example, "98/1.0" indicates that 98% mortality was observed using a 1.0 wt % AC formulation.

19

The compounds were generally tested at active compound concentrations of 1 wt % and below for agricultural and horticultural pests and at 5 wt % for structural pests (or to show activity). The carrier used in all formulations was T20, at one-fifth the concentration of the active compound. Blanks ("---") in Table XI indicate that the Active Compound was not tested against the pest listed.

In addition, evaluation of a 1 wt % phenyl salicylate formulation against the fungus, cladosporium, showed that this Active Compound was effective at both inhibiting fungal growth and at killing the fungus.

The protocols used were as follows:
Pharaoh Ants, Honey Bees, German Cockroaches, Cat Fleas and Houseflies All experiments were conducted with a hand held sprayer at an application rate equivalent to 100 gallons/acre. All reported mortality occurred at 24 hours post application ("HPA"). Specific treatment conditions were as follows: pharaoh ants were contained in paper cups with a cloth mesh enclosure at the top and sprayed from a distance of 12 inches; honey bees were contained in wire mesh cages with Petri dishes as end enclosures and sprayed from a distance of 24 inches; German cockroaches and houseflies were contained in Peet-Grady chambers and sprayed from a distance of 24 inches; and cat fleas were delivered onto carpet disks and sprayed from an un-reported distance.
Melon Aphids, Leafminers, Western Flower Thrips and Silverleaf Whiteflies For the melon aphids, western flower thrips and silverleaf whiteflies, the following protocol was used. Melon aphids, western flower thrips and silverleaf whiteflies were contained within a small arena with filter paper bottoms, and sprayed with 1 ml of formulation from a distance of 12–14 inches. Mortality of melon aphids was scored at 24 HPA and 48 HPA. Mortality of silverleaf whiteflies was assessed at 120 HPA and mortality of western flower thrips was scored at 72 HPA.

For the leafminers, the following protocol was used. Leafminers were allowed to infest chrysanthemum leaves. Infested leaves were then sprayed at the first sign of infestation with 100 ml of the formulation to drip. Leafminer mortality was scored at 20 days past infestation.
Melon Aphid and Two-spotted Spider Mite Plants (chrysanthemum and minirose) were infested with melon aphid and two-spotted spider mites and sprayed to run-off using a standard 250 ml hand-held sprayer. Mortality was recorded at 24 HPA and 48 HPA.

Benzyl salicylate was clearly shown to be insecticidal, with its activity on specific arthropods generally varying with the concentration of active compound.

Dose response testing was conducted using benzyl salicylate and benzyl benzoate on melon aphid, silverleaf whiteflies, leafminer and western flower thrips. Good dose response (response increasing with active compound concentration) was observed with benzyl benzoate (all except for western flower thrips). By contrast BS activity increased with AC concentration only on melon aphid. BS showed good dose response on Argentine ants, reaching an $LC_{100}$ at 1 wt % AC concentration, which held at 2 wt %, 3 wt % and 5 wt %.

The mode of action appears to be in the form of a contact insecticide, such as by disrupting membranes.

In evaluating efficacy against agricultural and horticultural pests, benzyl salicylate exhibited excellent activity on Argentine ants, although the compound can be phytotoxic to some plants. It is repellant to Argentine ants at one week and so will likely find utility in fruit orchards and green houses.

20

Also of particular note, is benzyl acetate, which demonstrated high activity on aphid and 2-spotted spider mites, but which has also been shown to be non-phytotoxic. For this reason, it will likely find utility in agriculture.

In evaluating efficacy against structural pests, BS was tested on pharaoh ant and cat flea at two concentrations, 1 wt % and 5 wt %. At 5 wt %, it was found to be effective on both pests, and may likely be active at lower concentrations. Since BS is GRAS and does not cause contact dermatitis (until 25 wt % concentration), it may find utility as an animal insecticide. ES was tested at 5 wt % concentration as both a contact spray and as a residual on American cockroach and proved to be lethal after a 3–7 minute direct spray.

Example 9

Pesticidal Activity of Ethyl Salicylate

The objective of the experiment was to evaluate the general effectiveness of ES in an emulsion formulation against the American cockroach.

An emulsion of ES (Sigma) was prepared at 5.0 wt % ES and 1.0 wt % T20. A 1 wt % T20 solution was also prepared as a formula blank treatment. A negative control of no treatment was included in the bioassay. The three treatments were applied to three replications of 4 cockroaches each.

The treatments were applied as sprays using a standard hand held 250 ml sprayer. For each direct treatment, 4 cockroaches were each sprayed to run-off on filter paper fitted to the bottom of a 1 liter stainless steel jar. Cockroaches were then transferred to 250 ml flasks for observation. For residuality/reintroduction bioassays, the treated filter papers were removed from direct treatment spray jars and allowed to air dry. After drying, the filter papers were replaced in jars and cockroaches introduced for observation.

Treatments and bioassay results are as follows:

TABLE XII

| Treatment | Lethality (%) | Time |
| --- | --- | --- |
| Direct spray | 100 | 3–7 minutes |
| Residuality/Reintroduction | 100 | 1–2 hours |
| Control (no treatment) | 8 | 24 hours |

Within 2 hours, both direct spray and residual/reintroduction proved lethal to all test cockroaches. The negative no treatment was acceptable as background mortality.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporate by reference.

The invention now having been fully described, it will be apparent to one of ordinary skill in the art that many changes and modifications can be made thereto without departing from the spirit or scope of the appended claims.

What is claimed:

1. A method for repelling ants from a plant, plant part, substrate, soil, material or object, which method comprises contacting the plant, plant part, substrate, soil, material or object with an effective amount of a composition comprising an agriculturally-acceptable carrier in combination with benzyl salicylate.

2. The method of claim 1 wherein the agriculturally-acceptable carrier comprises a surfactant.

3. The method of claim 2 wherein the surfactant is a polyoxyethylated sorbitol fatty acid ester.

4. The method of claim 2 wherein the surfactant is a polyethyleneglycol ether.

5. The method of claim 2 wherein said surfactant comprises 0.5 to 10% by weight of the composition.

6. The method of claim 1 wherein said composition is a concentrated product and benzyl salicylate is present in the amount of 25 to 50% by weight.

7. The method of claim 1 wherein said composition is a ready for use product and benzyl salicylate is present in the amount of 1 to 5% by weight.

* * * * *